US011208720B2

(12) United States Patent
Junkar et al.

(10) Patent No.: US 11,208,720 B2
(45) Date of Patent: Dec. 28, 2021

(54) METHOD FOR TREATMENT MEDICAL DEVICES MADE FROM NICKEL-TITANIUM (NITI) ALLOYS

(71) Applicant: JOZEF STEFAN INSTITUTE, Ljubljana (SI)

(72) Inventors: Ita Junkar, Ljubljana (SI); Rok Zaplotnik, Ljubljana (SI); Metka Bencina, Ajdovščina (SI); Miran Mozetic, Moravce (SI)

(73) Assignee: JOZEF STEFAN INSTITUTE, Ljubljana (SI)

( * ) Notice: Subject to any disclaimer, the term of this patent is extended or adjusted under 35 U.S.C. 154(b) by 3 days.

(21) Appl. No.: 16/594,858

(22) Filed: Oct. 7, 2019

(65) Prior Publication Data

US 2020/0109469 A1 Apr. 9, 2020

(30) Foreign Application Priority Data

Oct. 8, 2018 (EP) .................................... 18199209

(51) Int. Cl.
  *C23C 16/40* (2006.01)
  *A61L 31/02* (2006.01)
  *C23C 16/50* (2006.01)

(52) U.S. Cl.
  CPC .......... *C23C 16/405* (2013.01); *A61L 31/022* (2013.01); *C23C 16/50* (2013.01)

(58) Field of Classification Search
  CPC .................................................. C23C 16/405
  See application file for complete search history.

(56) References Cited

U.S. PATENT DOCUMENTS

| 5,591,227 | A | 1/1997 | Dinh et al. |
| 8,070,797 | B2 | 12/2011 | Flanagan et al. |
| 8,319,002 | B2 | 11/2012 | Daniels et al. |
| 2003/0175444 | A1 | 9/2003 | Huang et al. |

(Continued)

FOREIGN PATENT DOCUMENTS

| CN | 101294296 | * 10/2008 | ............. C25D 11/34 |
| CN | 101294296 | A | 10/2008 | |

(Continued)

OTHER PUBLICATIONS

EP Search Report dated Apr. 19, 2019, issued in counterpart International Application No. EP18199209.0 (7 pages).

*Primary Examiner* — Dah-Wei D. Yuan
*Assistant Examiner* — Andrew J Bowman
(74) *Attorney, Agent, or Firm* — Westerman, Hattori, Daniels & Adrian, LLP

(57) ABSTRACT

The present invention improves the surface modification of NiTi alloys used for instance in medical devices through treatment with hydrogen particles in a suitable gaseous discharge and with oxygen atoms. The technique according to the present invention provides the formation of biocompatible solely titanium oxide layer thus preventing nickel to be present in the top surface layer. Furthermore this enables nanostructuring of the surface which depends on the treatment conditions. Devices made from NiTi alloys treated with the method according to the present invention have improved biocompatibility; platelets do not readily attach and activate on such surfaces and the thrombus formation rate is reduced in comparison with extensively used untreated NiTi alloys.

18 Claims, 8 Drawing Sheets

(56) References Cited

U.S. PATENT DOCUMENTS

2006/0157159 A1 7/2006 Yeung et al.
2013/0129912 A1 5/2013 Cho et al.

FOREIGN PATENT DOCUMENTS

| CN | 102181903 A | 9/2011 |
| CN | 102425000 A | 4/2012 |
| ES | 2251312 A1 | 4/2006 |
| WO | 2015/200099 A1 | 12/2015 |

* cited by examiner

METHOD FOR TREATMENT MEDICAL DEVICES MADE FROM NICKEL-TITANIUM (NITI) ALLOYS

The present application claims priority to EP18199209, filed Oct. 8, 2018, the entire disclosure of which is incorporated herein by reference as though recited herein in full.

FIELD OF INVENTION

The present invention relates to a method for treatment of a medical device (which may be in contact with blood during usage) made from NiTi alloy, such as a stent or the like.

BACKGROUND OF THE INVENTION

Stents are commonly employed to enlarge the lumen wall and to restore the blood flow through the affected blood vessel. In addition to vascular applications, stents have been also employed in treatment of other body lumens including the gastrointestinal systems and the genital urinary systems. Vascular stents are made of hemocompatible and durable material, such as titanium (Ti), 316L stainless steel (SS-medical grade), Nitinol (an alloy of Nickel and Titanium) and Cobalt-Chromium (CoCr).

A vascular stent is mounted into a human blood vessel by a physician using a catheter. Once mounted the vascular stent is left in the blood vessel for years. The mechanical properties of the Nickel-Titanium (NiTi) alloys remain unchanged. A side effect, however, is chemical interaction between human blood and the NiTi alloys. The main risk is high platelet adhesion and activation (high possibility for thrombosis), as well as uncontrolled proliferation of smooth muscle cells which causes restenosis (narrowing of the vessel wall). Moreover, the placement of stent in the blood vessel is connected with mechanical injuries of the lumen wall, which initiates a variety of reactions, including platelet activation and thrombus formation, accompanied by inflammation, as well as proliferation and migration of smooth muscle cells within the media and the intima and restenosis due to neointimal hyperplasia. Conventional balloon angioplasty is associated with high rates of complications such as coronary dissection and elastic recoil. In some instances, a stent can elicit allergic reactions most commonly those that are containing Nickel, such as Nitinol and stainless steel. Vascular stents can be further divided into so-called bare metal stents (BMS) and the drug-eluting stents (DES). The BMS are not coated alloys, while the DES are coated alloys with various organic or inorganic coatings containing therapeutic agents, such as sirolimus, rapamycin and paclitaxel (U.S. Pat. No. 8,070,797B2), that inhibit tissue growth and reduce possibility of restenosis (for instance disclosed in U.S. Pat. No. 8,070,797B2, U.S. Pat. No. 5,591,227A). However, significant problems appeared on DES as these stents highly increase late-stent thrombosis, as normal endothelium growth on DES is inhibited. Moreover, the degradation products of polymers can be toxic. Recently it was observed that the long-term thrombosis rate in DES presents a huge problem and the death-rate of patients treated with DES compared to BMS is higher. Besides, the risk of early stent thrombosis can be decreased by using anti-platelet drugs (dual-anti-platelet therapy—DAPT), such as aspirin and P2Y12 antagonists that prevent clotting. However, patients taking DAPT are exposed to increased risk of fluid retention and hypertension and the risk of bleeding.

The ideal stent capable of overcoming all these clinical problems must have an anti-proliferative and anti-migratory effect on smooth muscle cells, but on the other hand must also enhance re-endothelialization—proliferation and migration of endothelial cells and platelet adhesion as well as activation. Although titanium and NiTi alloys are extensively used for stent applications, they still lack of desired biological responses. Therefore, the thrombogenicity and induced restenosis of blood-connecting devices remains a serious concern and should be given a great deal of attention in order to fabricate surfaces with improved tissue-material response. With the intention to enhance biocompatibility of NiTi alloys, modification of such surfaces with various polymer-free inorganic and organic (passive) coatings has increased rapidly. Besides, it has been shown that surface nanostructuring significantly affects the adhesion and activation of platelets (as disclosed in U.S. Pat. No. 8,319,002B2).

In order to improve surface properties of NiTi alloys, various surface modification techniques were suggested and applied, among them also methods for generating titanium oxide on NiTi alloy. However these methods are mainly based on arc oxidation (according to the disclosure of CN101294296 and CN102425000) or ion implantation, as explained bellow.

For example, ion implementation with argon/nitrogen plasma is disclosed in WO2004108983. In this case no hydrogen was used and the technique is based on plasma immersion ion implementation, where much higher powers of plasma are used, compared to the treatment disclosed in our application.

A similar plasma immersion ion implementation is disclosed for instance in US20060157159. In this case implementation of nitrogen, oxygen or carbon on the surface of NiTi alloy is achieved by plasma immersion ion implementation, or deposition or ion beam immersion or implementation. By such treatment improved biocompatibility of the surface and improved mechanical properties are achieved.

In another embodiment disclosed in US20030175444, coating the material surface with titanium oxide protective film or titanium oxide film containing H, Ta, Nb by plasma immersion ion implementation (PIII) is disclosed. The method includes using oxygen, which exists as plasma in the PIII vacuum chamber and the metal arc plasma source is used to create titanium plasma and allow for deposition of titanium atoms on the surface of inorganic or organic materials.

In CN102181903, improved biocompatibility of NiTi alloy was obtained by selective removal of Ni by anodic oxidation method by which titanium oxide film was formed. In this embodiment anodic oxidation was used and no plasma treatment is mentioned. The use of wet chemicals is necessary in this case and thus the method is also ecologically non friendly and time consuming.

According to CN102425000, a method for preparation of biologically active titanium dioxide film on NiTi alloy is disclosed. In this embodiment the micro-arc oxidation process in phosphoric acid is used and titanium oxide film with a nanoscale porous structure and good biocompatibility was fabricated on the NiTi alloy.

In another example according to WO2015200099 the NiTi alloy was coated by titanium dioxide nanotubes. In this example no plasma was used for modification. According to ES2251312 heat treatment was used for formation of stehiometric titanium oxide (TiO) with higher thickness compared to other classically applied treatments. In this case the NiTi alloy was subjected to thermal oxidation (<600° C., >20 min) at low pressure in order to promote preferential oxidation of Ti and formation of titanium oxide free from Ni in the surface of the alloy.

Therefore, many attempts have already been proposed to improve the surface properties of vascular stents made of NiTi for instance, but with limited success. Thus, there is a high demand to improve surface properties of NiTi alloys, especially those interacting with blood (like vascular stents). The implantation of currently available stents often induces inflammation responses, such as stent thrombosis, which still represents major concern in clinical practice. This condition is closely related to morphology and composition of implantable surfaces. Appropriate tuning of surface morphology and composition allows for reduced adhesion and activation of platelets and reduces the risk of thrombosis.

Hence, the object of the present invention is to provide an enhanced method for surface treatment of devices, especially stents or the like.

SUMMARY OF THE INVENTION

The present invention is defined by the appended independent claims.

According to the present invention a method for treatment of a medical device or a blood connecting device made from a NiTi alloy, such as stent or the like, is disclosed. Blood connecting device may be an implantable device which can be used for a human or an animal host. These devices may come in direct contact with blood of a patient but also other devices like for instance for orthopaedic usage may make use of the method according to the present invention.

In a first step mounting said device made from NiTi alloys into a reaction chamber is provided. Mounting means that the device is introduced into a dedicated chamber. It is conceivable that the device is fixed by some fixing means but also other techniques are possible. In a next step evacuating said reaction chamber to achieve pressure below atmospheric pressure, preferably in a range between about 0.1 Pa to about 1 Pa is performed. This step is crucial for the later step where the discharge, is generated and maintained.

Then leaking of hydrogen gas into said reaction chamber during continuous pumping of said reaction chamber so that the pressure in the said reaction chamber is between 1 and 100 000 Pa, preferably, between 10 and 1000 Pa is provided and subsequently an electrical discharge in the said reaction chamber filled with said hydrogen is established. According to an embodiment it may be conceivable that the leaking of hydrogen gas is performed in a continuous manner. This ensures a proper electrical discharge condition.

In a next step reacting of said device made from NiTi alloys with gaseous particles created in hydrogen upon excitation of said hydrogen molecules by said electrical discharge is provided. This step is maintained until the native oxide on the surface of the device to be treated is eliminated. Therefore, the device is now completely free of native oxide and thus ready to be treated according to the present invention. Further introducing neutral oxygen atoms into said reaction chamber is provided. In said reaction chamber the parallel reactions of said neutral oxygen atoms and gaseous particles created in hydrogen discharge take place with said device made from NiTi alloys. This step ensures optimal conditions for the method according to the present invention.

According to the invention, where said simultaneous reactions take place until a pure titanium oxide film is established on the surface of said device made from NiTi alloys. This titanium film has dedicated dimensions for the purpose of the treated device.

Finally, the method ends by turning off said electrical discharge in said treatment chamber, closing inlet of said gases and venting said treatment chamber with essentially dry air.

Thus, the present invention improves the surface modification of NiTi alloys through treatment with hydrogen particles and oxygen gas in a suitable gaseous discharge. The technique according to the present invention provides the formation of protective solely titanium oxide layer and consequently reduced Ni concentration on the surface and enables nanostructuring depending on the treatment conditions. NiTi alloys devices treated with the method according to the present invention have improved biocompatibility; platelets do not readily attach and activate on such surfaces and the thrombus formation rate is reduced in comparison with extensively used untreated NiTi alloys.

Therefore, the present invention avoids deposition of oxide films or application of energetic ions to form oxide films on the surface of materials made from NiTi alloys. Moreover it provides a method for improved biocompatibility of materials made from NiTi alloys by treatment of surfaces in hydrogen gas, said hydrogen gas subjected to an electrical discharge, with continuous addition of excited oxygen atoms. By this, removal of Ni oxides from the surface is achieved and high quality titanium oxide film is formed on the surface. The efficiency of the method, which is the subject of this invention, has been confirmed by Electron Spectroscopy for Chemical Analysis (ESCA) technique, which enables detection of the chemical composition of the surface or by etching the surface and also offers the possibility to analyse the depth profile of the material.

Against the state of the art, the method of invention enables a formation of a high-quality titanium oxide layer, which is free of Nickel or nickel oxides. The compactness of the oxide film enables improved biocompatibility of products made from NiTi alloys. The method of invention allows for adjusting the thickness of the titanium oxide film thus solving a particular problem of cracking said oxide film in case of low thickness, what would otherwise cause slow but continuous release of nickel in real environment, i.e. during contact of said products made from NiTi alloys with human blood.

The biocompatibility of the materials made from NiTi alloys treated with the method of invention is further confirmed by their behaviour in biological environment, more particularly by interaction with platelets. The treatment with the method of invention allows for NiTi alloys' surface to become nanostructured. It has been previously shown that surface nanostructuring could be beneficial for biocompatibility improvement. The interactions between NiTi alloys and platelets are observed with Scanning Electron Microscopy (SEM) and it is obvious that significant change in platelet adhesion and activation is observed after treatment of NiTi alloy with the method of invention. Biocompatibility of alloys after treatment by the method of invention is significantly improved, since decreased platelet adhesion and activation on NiTi alloys is observed.

According to an embodiment said hydrogen gas leaking is amended with an additional gas, preferably a noble gas. Such conditions enable higher reactive particle densities. Under these conditions an amended oxide thickness and surface nanostructure has been observed.

According to an embodiment, the electrical discharge causes gas to transform into the non-equilibrium gas state.

According to an embodiment the simultaneously reacting is maintained until said titanium oxide film provides a thickness of 30 to 1200 nm, preferably 60 to 800 nm and especially 80 to 700 nm. For the later use of the device, like a vascular stent, a thickness of around 80 nm may be preferred.

BRIEF DESCRIPTION OF THE DRAWINGS

The invention is herein described, by way of example only, with reference to the accompanying drawings, wherein.

DETAILED DESCRIPTION OF THE INVENTION

Figure 1:
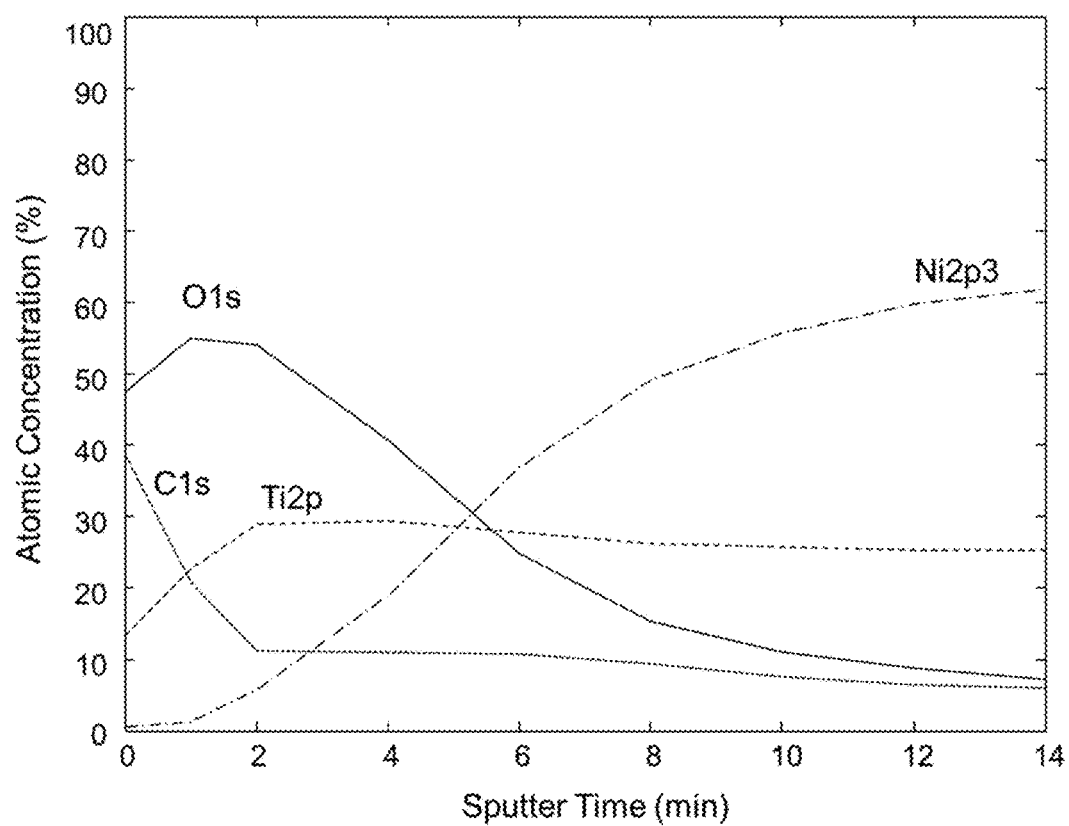
FIG. 1 shows ESCA profile of a virgin sample made from NiTi alloy used for vascular stents.

Vascular stents are commonly employed in case of cardiovascular diseases, where there is a need to enlarge the lumen wall and to restore the blood flow. A vascular stent is mounted into a human blood vessel by a physician using a catheter. The stent materials should have appropriate mechanical properties and satisfactory biocompatibility and hemocompatibility. Stents are made of titanium (Ti), 316L stainless steel (SS-medical grade), Nitinol (NiTi alloy) and Cobalt-Chromium (CoCr). However, the drawback connected with this type of vascular implants still remains due to high risk of restenosis and thrombosis. In case of NiTi and SS vascular stents, there is a risk of allergenic reactions due to release of Nickel. However, these materials are frequently employed due to their excellent mechanical properties and long-term durability. The mechanical properties of the NiTi alloys remain unchanged for ages.

New generation of so-called drug eluting stents (DES) has been developed to overcome the above-mentioned limitations. Therefore, the bare metal stents (BMS) were coated with anti-cell-proliferative coatings in order to prevent uncontrolled proliferation of smooth muscle cells (reducing the risk of restenosis) or anti-thrombotic drugs that reduce the risk of thrombosis. Unfortunately, long-term studies of DES have shown to increase the risk of thrombosis, mainly due to insufficient proliferation of endothelial cells that line the inner side of our natural blood vessels and are thought to be an ideal anti-thrombogenic material. Thus, novel approach to improve surface properties of vascular stents is still needed and is solved by the method according to the present invention.

According to the present invention, the improved biocompatibility/hemocompatibility is achieved by treatment of NiTi alloy with reactive hydrogen particles created in a suitable gaseous discharge and subsequent addition of neutral oxygen atoms. Such a treatment allows for the formation of high-quality titanium oxide layer on the surface of materials made from NiTi alloy, the oxide films containing only titanium oxide thus being free from nickel or nickel oxides. This significantly reduces adhesion and activation of platelets on the surface and reduces the risk of thrombosis.

The simplest method for formation of oxide film on a metallic surface is thermal oxidation. Thermal oxidation stands for heating of a metal in an atmosphere containing oxygen. The thickness of the oxide film, achieved by thermal oxidation, depends on the nature of the metal, the treatment time at elevated temperature, the temperature of the metal during exposure to oxygen-containing atmosphere and the partial pressure of oxygen in said oxygen-containing atmosphere. Such a treatment therefore allows for achieving a practically arbitrary thickness of the oxide film on the metallic surface, depending on the chosen treatment conditions. A drawback of thermal oxidation is reflected from the fact that the oxide film usually contains a mixture of different oxides. In the case the metal is a NiTi alloy the oxide film contains both titanium and nickel oxides.

According to the present invention, a uniform titanium oxide film is obtained by an alternative treatment. Instead of heating materials made from NiTi alloys in oxygen-containing atmosphere, the material made from NiTi alloys are treated using different gases in the right manner.

In the first step, according to the present invention, the NiTi alloy is mounted into an appropriate reacting chamber, which is capable of withstanding evacuation. Once the reaction chamber is evacuated to a low pressure, preferably below few Pascal, it is filled with hydrogen. The purpose of hydrogen is to interact with the native nickel oxide layer and reduce it to oxygen-free nickel. Such reactions are unlikely to occur at reasonably low temperature in hydrogen gas under normal conditions. In order to facilitate reduction of the native nickel oxide, an appropriate gaseous discharge is created in hydrogen gas present in the reaction chamber. In the gaseous discharge, hydrogen is transferred into a state of non-equilibrium gas. In hydrogen discharge, neutral hydrogen molecules are dissociated to atoms and partially ionized. Both neutral hydrogen atoms as well as molecular and atomic hydrogen ions are chemically much more reactive at given temperature then hydrogen molecules under normal conditions and interact with metal oxides. The interaction is essentially selective: the neutral hydrogen atoms as well as molecular and atomic hydrogen ions will preferentially react chemically with oxides of lower binding energy. In the case of materials made from NiTi alloys, the neutral hydrogen atoms as well as molecular and atomic hydrogen ions will react preferentially with nickel oxide. The chemical interaction leads to reduction of nickel oxide to pure metallic nickel following the reaction, which could be schematically presented as NiO+2H→Ni+H$_2$O. The resulting water molecule is desorbed from the surface and removed from the reaction chamber due to continuous pumping of said reaction chamber. The treatment with hydrogen discharge therefore leads to a modification of the original native oxide film: instead of a mixture of titanium and nickel oxides, a mixture of titanium oxides and metallic nickel is achieved. Such a surface condition is not stable and will immediately change to its original state when exposed to air. In order to avoid this effect, the materials made from NiTi alloys essentially remain in the reaction chamber according to the present invention.

Once the nickel is reduced from oxide to metallic nickel an additional step is realized. Without breaking treatment with hydrogen discharge, neutral oxygen atoms (in the ground state and/or in the first excited state commonly referred to as O($^1$D) state) are introduced into the reaction chamber. The neutral oxygen atoms are chemically extremely reactive and will cause oxidation of almost all metals. In the case of NiTi alloys, both titanium and nickel oxidize upon exposure to neutral oxygen atoms. Nickel oxides, however, will be quickly reduced to metallic nickel due to reaction schematically presented as NiO+2H→Ni+H$_2$O, while titanium oxide will be more stable. Simultaneous application of hydrogen discharge and neutral oxygen atoms therefore assures for oxidation of titanium while leaving nickel essentially in the metallic form. Due to extensive interaction between neutral oxygen atoms and materials made from NiTi alloys, the net effect of simultaneous application of hydrogen discharge and neutral oxygen atoms will be growth of titanium oxide film on the surface of said NiTi alloys. Titanium atoms will diffuse toward the surface and oxidize resulting in depletion of the surface layer from nickel. If the flux of neutral oxygen atoms is low, the oxide film will be thin but free of nickel. Once the very thin but uniform titanium oxide film is made due to interaction with neutral oxygen atoms, nickel will not be able to appear on the surface of treated materials made from NiTi alloys due to very poor mobility of nickel in titanium oxide materials. Increasing the flux of neutral oxygen atoms onto the samples will allow for thickening of the titanium oxide film free from nickel since the mobility of nickel in compact titanium oxide film is very poor. Upon treatment with appropriate fluence of neutral oxygen atoms, a rather thick pure titanium oxide film is formed on the surface of materials made from NiTi alloys. The film of titanium oxide grown on the NiTi alloys upon treatment according to present invention is extremely stable since interaction of materials with neutral oxygen atoms allow for synthesizing very compact and dense oxide films. The inertness and long-term stability of titanium oxide films grown on the NiTi alloys has a significant influence on biocompatibility/hemocompatibility of the surface. Moreover, by varying the fluence of neutral oxygen atoms, the thickness of titanium oxide layer and surface nanotopography can be controlled. The efficiency of the present invention will be shown in the following examples.

Example 1: A Virgin NiTi Alloy Used for Stent Application

In the example disclosed herein, a virgin NiTi alloy used for stent was analyzed by Electron Spectroscopy for Chemical Analysis (ESCA) method in order to obtain information about chemical composition in-depth. To determine chemical composition in-depth, the Ar$^+$ ion beam with 1 keV energy was used for sputtering at an incidence angle of 45° and a raster of 5 mm×5 mm. The sputtering rate was approximately 1 nm/min. Depth profile obtained from ESCA is presented in FIG. 1. The results indicate that Ni is also detected on the top surface (about 1 at. %) and its concentration is slowly increasing in depth. The analysis of depth profile spectra indicates that the natively formed titanium oxide is present on the top surface (about 5 nm thick) and an increase in concentration of nickel and its oxides is slowly observed. This indicates that a very thin native titanium oxide film is formed on NiTi alloy used for stent application.

The adhesion and activation of platelets on a virgin NiTi alloy used for stent was done according to the following procedure. Prior to whole blood incubation virgin NiTi surfaces were cleaned with ethanol, dried and incubated with whole blood taken by vein puncture from a healthy human donor. Virgin NiTi samples were incubated for 30 min with whole blood. The blood was drawn into 9 ml tubes with tri sodium citrate anticoagulant (Sigma). Afterwards, the fresh blood was incubated with NiTi surfaces in 24 well plates for 1 hour at room temperature and at gentle shaking at 300 RPM. The sample was incubated with 1 ml of whole blood. After 1 h of incubation, 1 ml of phosphate-buffered saline (PBS) was added to the whole blood. The blood with PBS was then removed and the titanium surface was rinsed 5 times with 2 ml PBS in order to remove weakly adherent platelets. Adherent cells were subsequently fixed with 400 μl of 1 PFA (paraformaldehyde) solution for 15 min at room temperature. Afterwards, the surfaces were rinsed with PBS and then dehydrated using a graded ethanol series (50, 70, 80, 90, 100 and again 100 vol. % ethanol) for 5 min and in the last stage in the series (100 vol. % ethanol) for 15 min. Then the samples were placed in a Critical Point Dryer, where the solvent is exchanged with liquid carbon dioxide. By increasing the temperature in the drier, the liquid carbon dioxide passes the critical point, at which the density of the liquid equals the density of the vapour phase. This drying process preserves the natural structure of the sample and avoids surface tension, which could be caused by normal drying. The dried samples were subsequently coated with gold and examined by means of SEM (Carl Zeiss Supra 35 VP) at accelerating voltage of 1 keV. Evaluation of platelet adhesion and activation from SEM images was done according to the morphology and number of platelets. Morphological forms of platelets from the least activated to the most activated are as follows: round (R)>dendritic (D)>spread dendritic (SD)>spread (S)>fully spread (FS).

Figure 3:
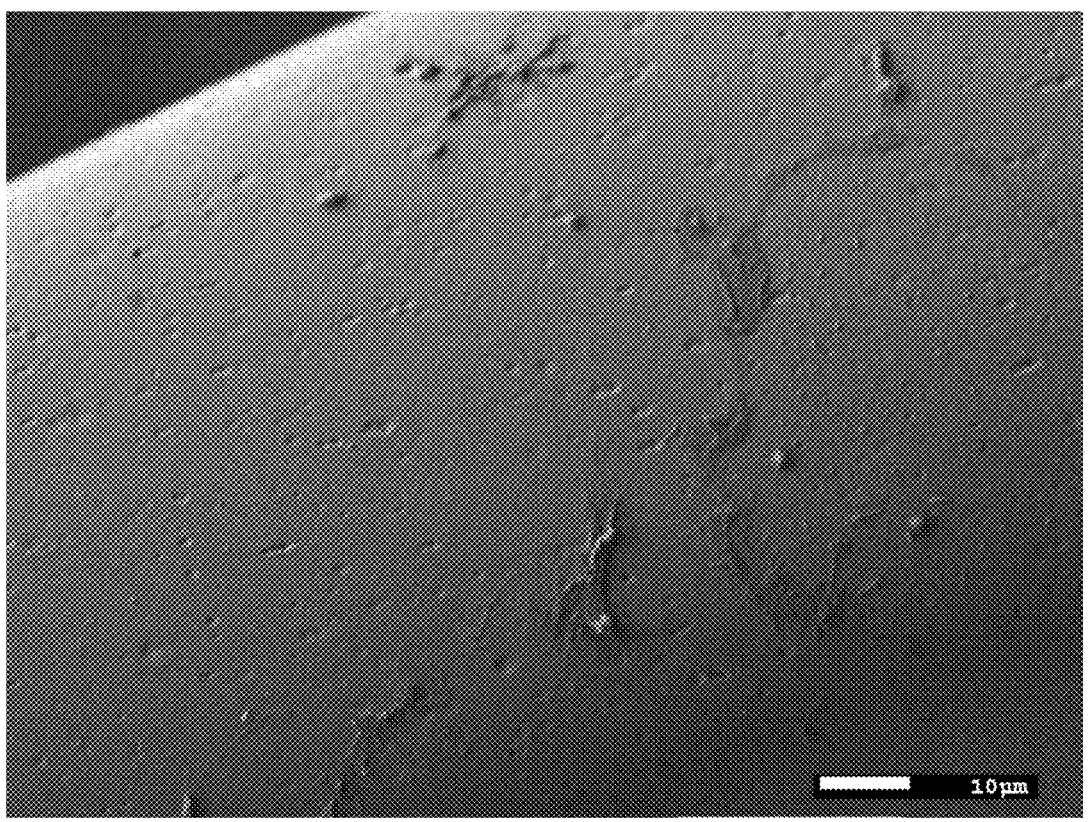
FIG. 3 shows an SEM image of a virgin vascular stent made from NiTi alloy after incubation with whole blood (magnification 500×)
Figure 4:
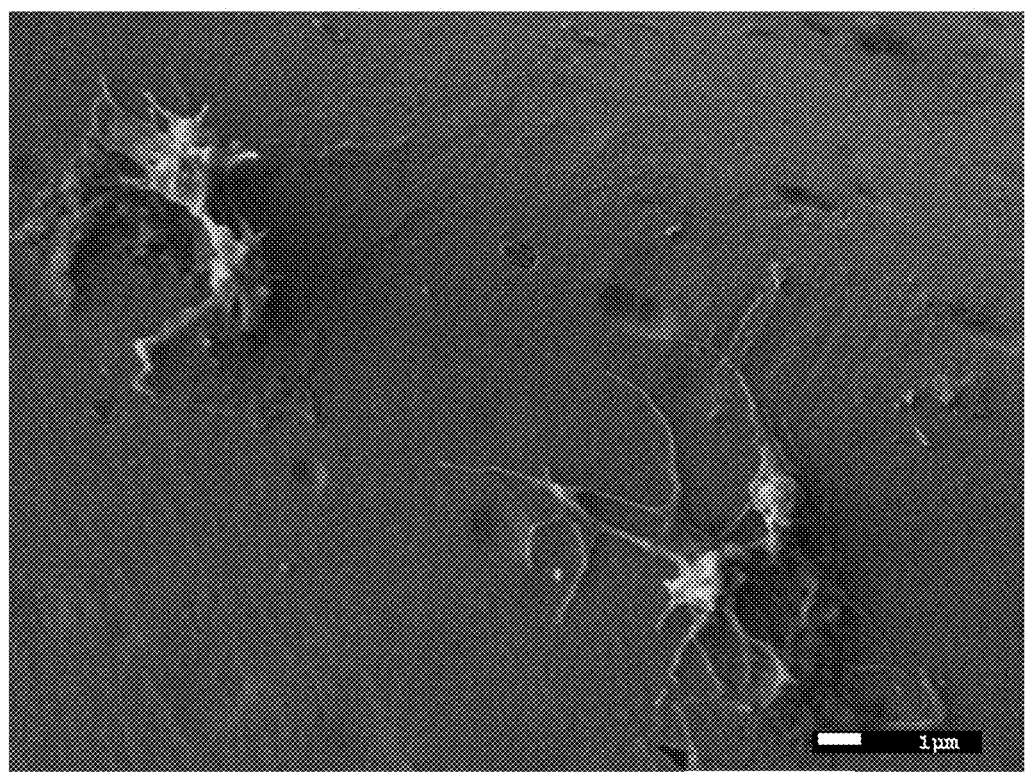
FIG. 4 shows an SEM image of a virgin vascular stent made from NiTi alloy after incubation with whole blood (magnification 1.000×)

Differences in adhesion of platelets were observed from SEM images as seen in FIG. 3 and FIG. 4. Platelet adhesion and activation can be determined by counting the number of attached cells as well as by observing the morphological changes of platelets on the surface. Results from SEM analysis clearly indicate that platelets attach and activate on the surface of the NiTi alloy used for stent application. In FIG. 4, taken at higher magnification, the morphology of platelets can be studied. It can be observed that platelets on the surface are in dendritic, spread and fully spread form, which is correlated with high platelet activation on the surface. Such morphology of platelets has high potential to cause thrombosis and reduces the life of such virgin NiTi alloy used for stent application.

Example 2: NiTi Alloy Used for Stent Application after Treatment According to the Method of the Present Invention where the Fluence of Neutral Oxygen Atoms was Set to 1×10$^{24}$ m$^{-2}$ NiTi alloy used for stent application was treated according to the present invention where the fluence of neutral oxygen atoms was set to $1 \times 10^{24}$ m$^{-2}$, while the flux was set to $2 \times 10^{23}$ m$^{-2}$ s$^{-1}$. The surface was analyzed by Electron Spectroscopy for Chemical Analysis (ESCA) method in order to obtain information about chemical composition in-depth. To determine chemical composition in-depth, the Ar$^+$ ion beam with 1 keV energy was used for sputtering at an incidence angle of 45° and a raster of 5 mm×5 mm. The sputtering rate was approximately 1 nm/min. Depth profile obtained from ESCA is presented in FIG. 2, whereby no nickel was detected on the top surface layer.

The sample was mounted into the reaction chamber, the chamber was evacuated to a pressure below the detection limit of the pressure gauge (the pressure limit was about 1 Pa), the reaction chamber was filled with hydrogen during continuous pumping so the hydrogen pressure in the system was 30 Pa. A radiofrequency discharge of power 500 W was established in the reaction chamber filled with hydrogen at the pressure of 30 Pa. The sample was left to react with reactive hydrogen particles created in hydrogen gas under discharge conditions for 10 s. After the period of 10 s, neutral oxygen atoms were slowly but continuously leaked into the reaction chamber during further continuous operation of the electrical discharge. The fluence of neutral oxygen atoms on the surface of the sample made from NiTi surface used for vascular stents was set to $1 \times 10^{24}$ m$^{-2}$.

Figure 2:
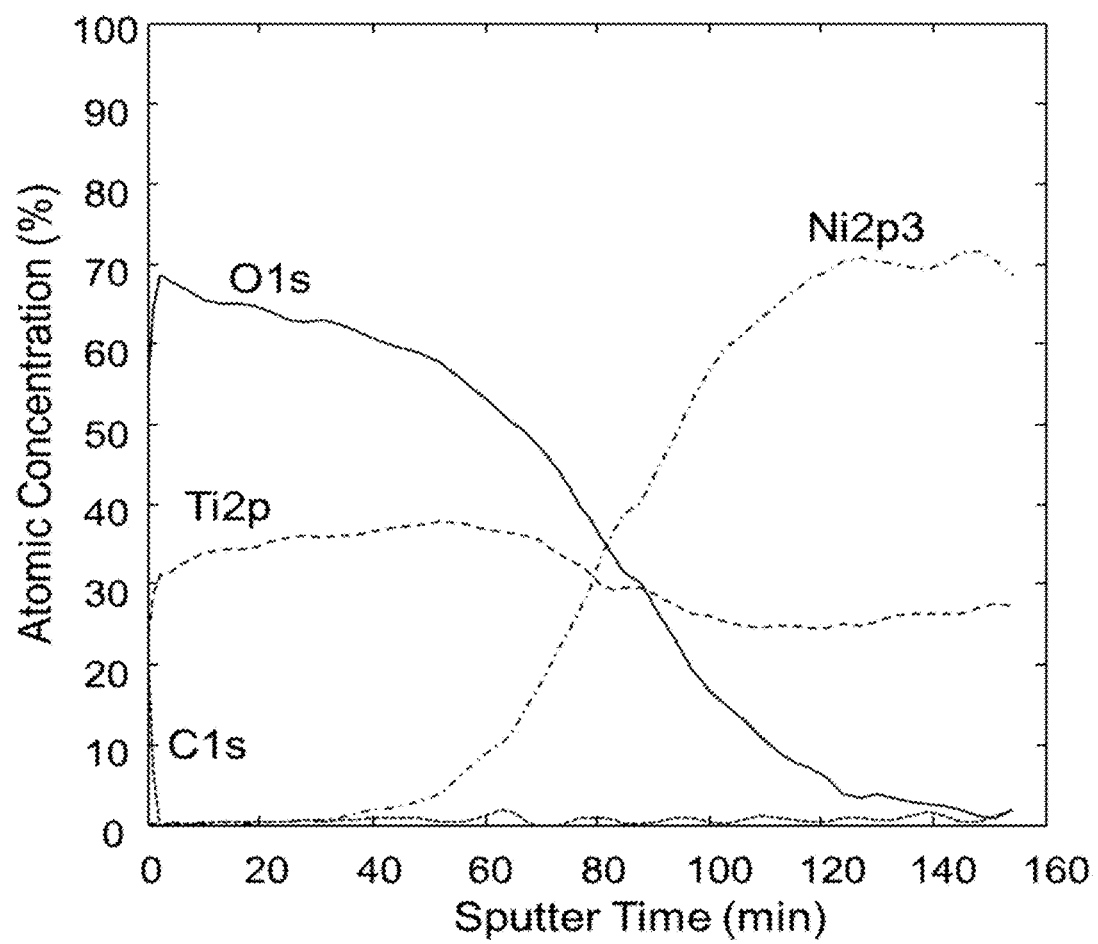
FIG. 2 shows ESCA profile of a sample made from NiTi alloy after treatment by the method of invention, where the fluence of neutral oxygen atoms were set to $1\times10^{24}$ $m^{-2}$, while flux was set to $2\times10^{23}$ $m^{-2}$ $s^{-1}$.

Results of chemical composition in-depth are presented in FIG. 2. The results indicate that Ni was not detected on the top surface (less than 0.2 at. %). It could be evaluated that after treatment by the method of invention about 80 nm thick titanium oxide films is formed on the surface.

Figure 5:
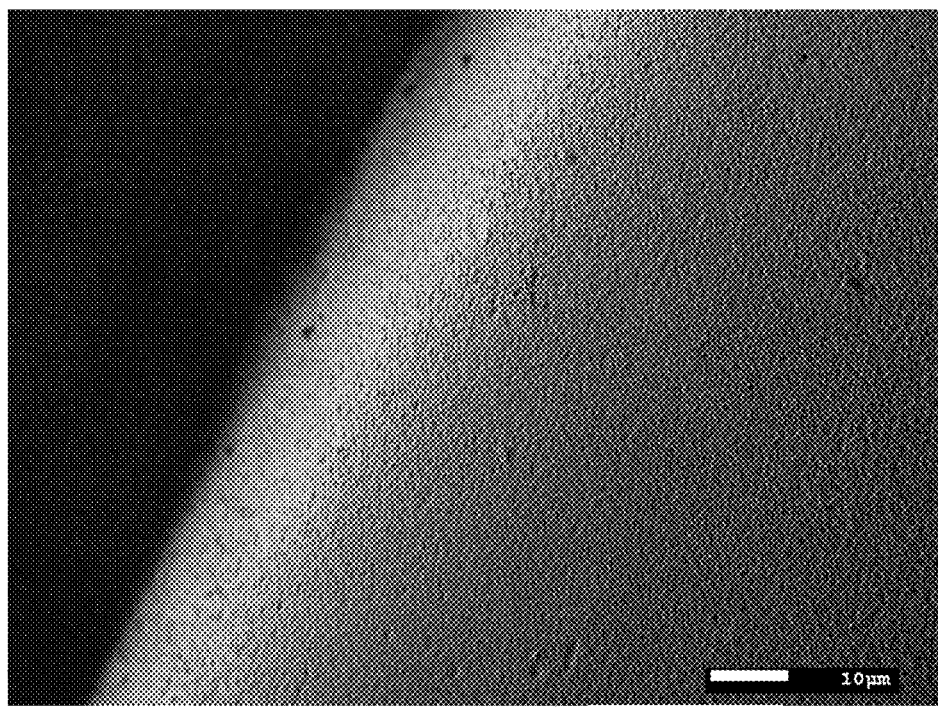
FIG. 5 shows an SEM image of a vascular stent made from NiTi alloy after treatment by the method of invention, where the fluence of oxygen atoms was set to $4\times10^{22}$ $m^{-2}$ while the flux was set to $2\times10^{23}$ $m^{-2}$ $s^{-1}$ (magnification 500×)
Figure 6:
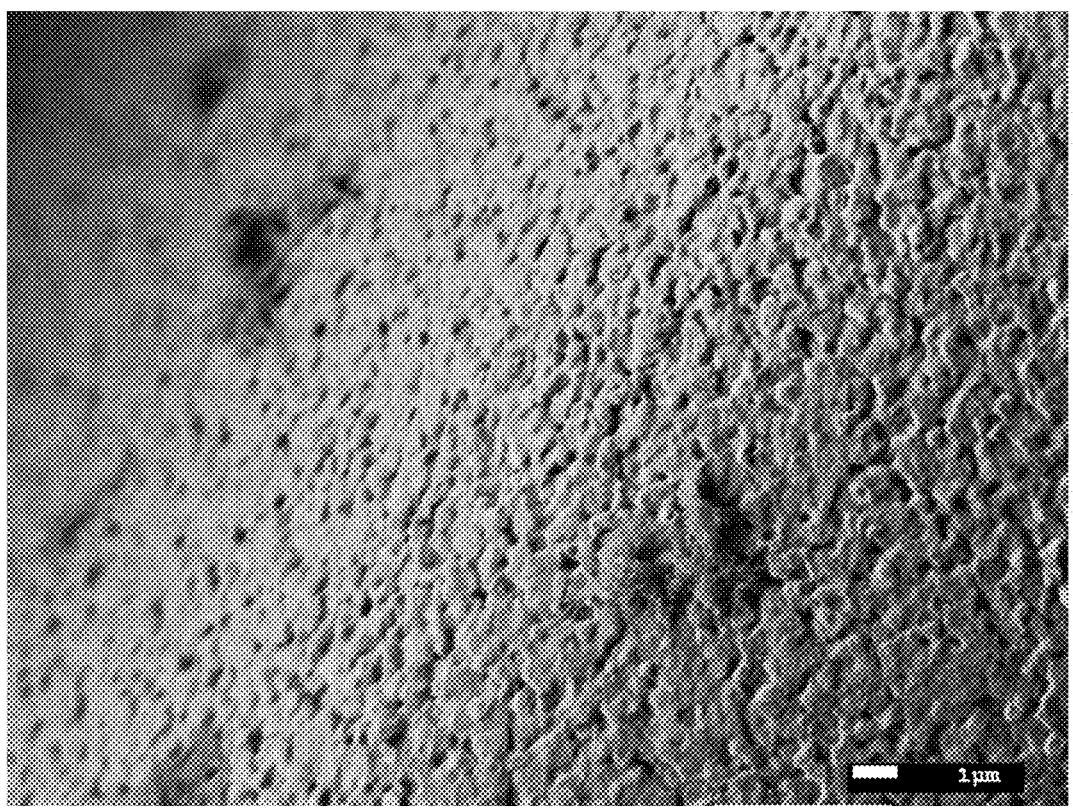
FIG. 6 shows an SEM image of a vascular stent made from NiTi alloy after treatment by the method of invention, where the fluence of oxygen atoms was set to $1\times10^{24}$ $m^{-2}$ while the flux was set to $2\times10^{23}$ $m^{-2}$ $s^{-1}$ and the sample was incubated with whole blood (magnification 1.000×)

The studies on adhesion and activation of platelets were conducted on NiTi alloy surface used for stent application immediately after treatment according to the present invention where the fluence of neutral oxygen atoms was set to $1 \times 10^{24}$ m$^{-2}$. The incubation procedure with whole blood was the same as the one described in Example 1. The images of SEM analysis at lower and higher magnification are presented in FIG. 5 (where only a few platelets were observed on the surface and they were preferentially in the round non-activated state) and FIG. 6, respectively. With reference to FIG. 6 it was hard to detect platelets on the surface, however, those that were detected, were in round non-activated form. The surface morphology after treatment by the method of invention is altered and grain-like morphology is formed on the surface.

SEM analysis clearly showed that less platelets adhere on NiTi alloy used for stent application after treatment of the surface by the method of invention, where the fluence of neutral oxygen atoms was set to $1 \times 10^{24}$ m$^{-2}$. There are almost no platelets detected on the surface, while those that can be found are mainly in less active form—round and dendritic as seen at higher magnification (FIG. 6). Such surfaces will, to a lesser extent, elicit undesired thrombus formation in comparison to the samples prepared in Example 1. Moreover, the altered surface morphology obtained according to the present invention can be observed in FIG. 6. The surface seems to be nanostructured and small nano-grooves are uniformly formed on the surface, which may also influence on platelet adhesion and activation.

Example 3: NiTi Alloy Used for Stent Application after Treatment by the Method of Invention where the Fluence of Neutral Oxygen Atoms was Set to $4 \times 10^{24}$ m$^{-2}$ NiTi alloy used for stent application was treated according to the present invention where the fluence of neutral oxygen atoms was set to $4 \times 10^{24}$ m$^{-2}$, while the flux was set to $2 \times 10^{23}$ m$^{-2}$ s$^{-1}$. In this case, a sample was mounted into the reaction chamber, the chamber was evacuated to a pressure below the detection limit of the pressure gauge (the pressure limit was about 1 Pa), the reaction chamber was filled with hydrogen during continuous pumping so the hydrogen pressure in the system was 30 Pa. A radiofrequency discharge of power 500 W was established in the reaction chamber filled with hydrogen at the pressure of 30 Pa. The sample was left to react with reactive hydrogen particles created in hydrogen gas under discharge conditions for 10 s. After the period of 10 s, neutral oxygen atoms were slowly but continuously leaked into the reaction chamber during further continuous operation of the electrical discharge. The fluence of neutral oxygen atoms on the surface of the sample made from NiTi surface used for vascular stents was set to $4 \times 10^{24}$ m$^{-2}$.

The studies on adhesion and activation of platelets were conducted on NiTi alloy surface used for stent application immediately after treatment by the method of invention where the fluence of neutral oxygen atoms was set to $4 \times 10^{24}$ m$^{-2}$. The incubation procedure with whole blood was the same as the one described in Example 1.

Figure 7:
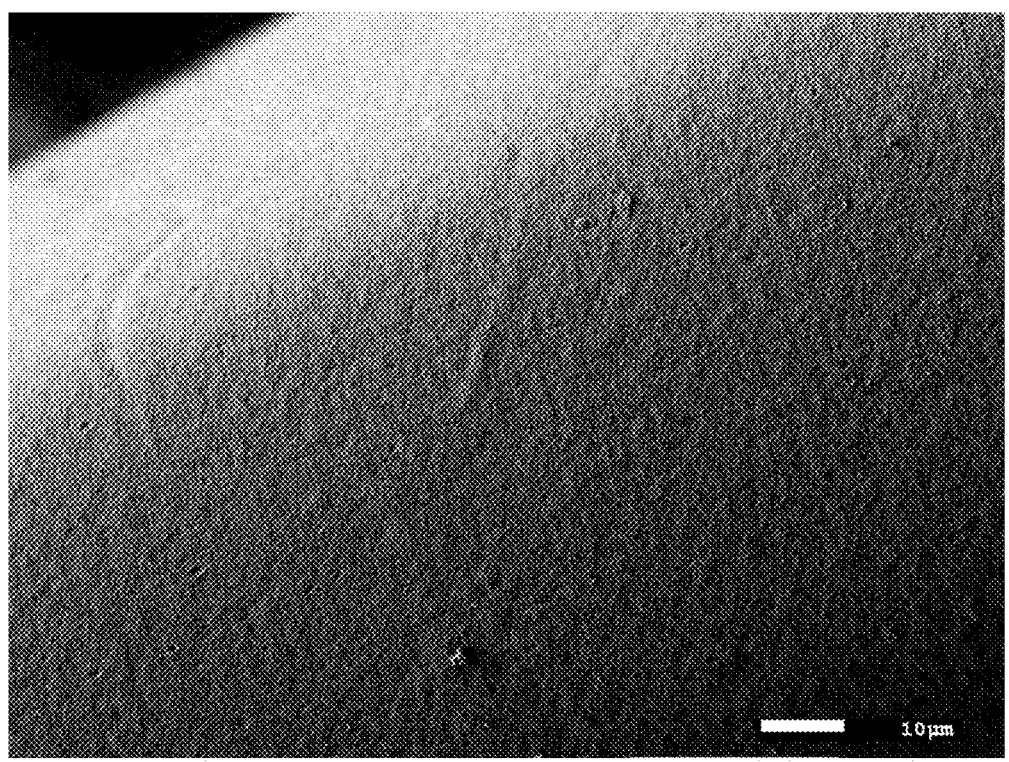
FIG. 7 shows an SEM image of a vascular stent made from NiTi alloy after treatment by the method of invention, where the fluence of oxygen atoms was set to $4\times10^{24}$ $m^{-2}$ while the flux was set to $2\times10^{23}$ $m^{-2}$ $s^{-1}$ and the sample was incubated with whole blood (magnification 500×)
Figure 8:
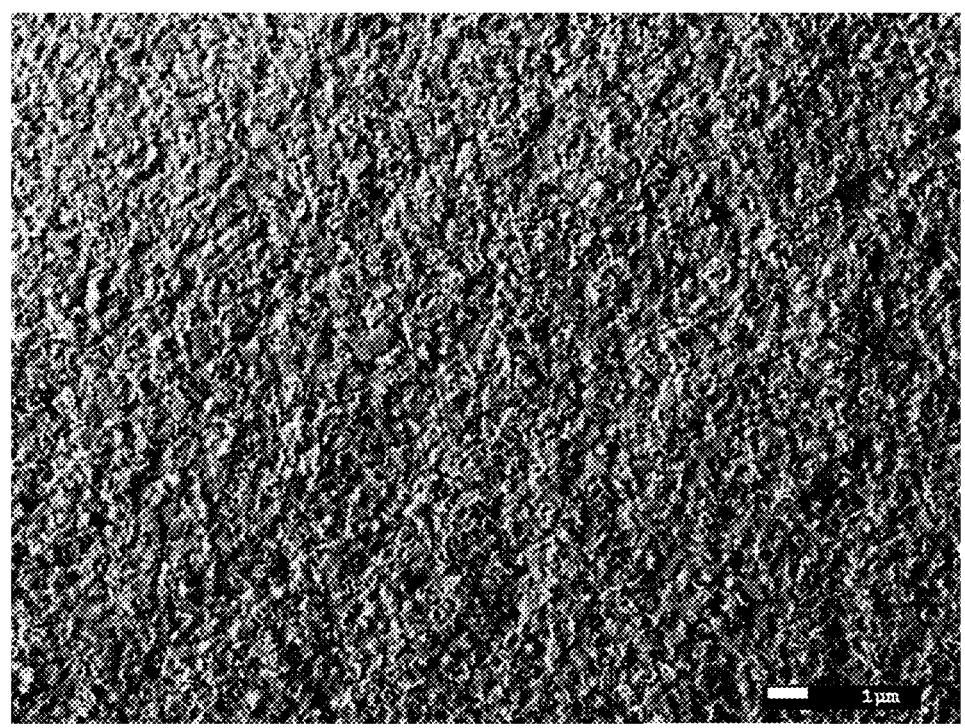
FIG. 8 shows an SEM image of a vascular stent made from NiTi alloy after treatment by the method of invention, where the fluence of oxygen atoms was set to $4\times10^{24}$ $m^{-2}$ while the flux was set to $2\times10^{23}$ $m^{-2}$ $s^{-1}$ and the sample was incubated with whole blood (magnification 1.000×).

The images of SEM analysis at lower and higher magnification are presented in FIGS. 7 and 8, respectively. The images at higher magnification shows that the surface has grain-like surface morphology, which increases surface area and surface roughness, hence no platelets were detected on the surface.

According to SEM analysis of samples treated by the method according to the invention where the fluence of neutral oxygen atoms was set to $4 \times 10^{24}$ m$^{-2}$, platelet adhesion was prevented, no platelets could be detected on the surfaces prepared by this method as seen from lower magnification image in FIG. 7.

At higher magnification image shown in FIG. 8, the nano-structured surface can be observed. Compared to surface in Example 2 presented in FIG. 6 it can be clearly seen that nano-groves in FIG. 8 are much more pronounced, which could further reduce adhesion and activation of platelets on such surfaces. Surfaces treated according to the present invention, where the fluence of neutral oxygen atoms was set to $4 \times 10^{24}$ m$^{-2}$, could serve as blood connecting devices or medical devices to be implanted and having direct contact with blood of a host, such as vascular stents with superior properties.

Finally, it can be stated that the present invention optimizes the biocompatibility of materials and products or devices made from NiTi alloys in contact with blood, especially vascular stents for instance. Against the background, the method allows for formation of pure titanium oxide film on the surface of NiTi alloys, which significantly reduces activation and adhesion of platelets and reduces the risk of thrombosis.

Although specific embodiments have been illustrated and described herein, it will be appreciated by those of ordinary skill in the art that a variety of alternate and/or equivalent implementations may be substituted for the specific embodiments illustrated and described without departing from the scope of the present invention. This application is intended to cover any adaptations or variations of the specific embodiments discussed herein.

Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. Method for treatment a medical device made from a NiTi alloy, comprising:
    mounting said device made from NiTi alloys into a reaction chamber;
    evacuating said reaction chamber to achieve pressure below atmospheric pressure;
    leaking hydrogen gas into said reaction chamber during continuous pumping of said reaction chamber so that the pressure in the said reaction chamber is between 1 and 100 000 Pa;
    establishing an electrical discharge in the said reaction chamber filled with said hydrogen;
    reacting said device made from NiTi alloys with gaseous particles created in hydrogen upon excitation of said hydrogen molecules by said electrical discharge until the native oxide is eliminated;
    introducing neutral oxygen atoms into said reaction chamber;
    simultaneously reacting said device made from NiTi alloys with said neutral oxygen atoms in said reaction chamber and with gaseous particles created in hydrogen upon excitation of said hydrogen by said electrical discharge until a titanium oxide film is established on the surface of said device made from NiTi alloys; and
    turning off said electrical discharge in said treatment chamber, closing inlet of said gases and venting said treatment chamber with essentially dry air.

2. Method according to claim 1, wherein said hydrogen gas leaking is amended with an additional gas.

3. Method according to claim 1, wherein said electrical discharge is selected from the list of discharges including DC (Direct Current), AC (Alternative Current), RF (Radio-Frequency) and MW (Micro Wave) discharges.

4. Method according to claim 1, further comprising increasing the concentration of said neutral oxygen atoms in said reaction chamber during parallel reacting of said device made from NiTi alloys with gaseous particles created in hydrogen upon excitation of said hydrogen gas by said electrical discharge.

5. Method according to claim 1, wherein said electrical discharge causes gas to transform into a non-equilibrium state.

6. Method according to claim 1, wherein said simultaneous reaction is maintained until said titanium oxide film with a thickness of 40 to 1000 nm.

7. Method according to claim 1, wherein the fluence of said neutral oxygen atoms onto said device made from NiTi alloys in said reaction chamber is between $1 \times 10^{19}$ m$^{-2}$ and $1 \times 10^{25}$ m$^2$.

8. Method according to claim 2, wherein said electrical discharge is selected from the list of discharges including DC (Direct Current), AC (Alternative Current), RF (Radio-Frequency) and MW (Micro Wave) discharges.

9. Method according to claim 2, further comprising increasing the concentration of said neutral oxygen atoms in said reaction chamber during parallel reacting of said device made from NiTi alloys with gaseous particles created in hydrogen upon excitation of said hydrogen gas by said electrical discharge.

10. Method according to claim 3, further comprising increasing the concentration of said neutral oxygen atoms in said reaction chamber during parallel reacting of said device made from NiTi alloys with gaseous particles created in hydrogen upon excitation of said hydrogen gas by said electrical discharge.

11. Method according to claim 2, wherein said electrical discharge causes gas to transform into a non-equilibrium state.

12. Method according to claim 3, wherein said electrical discharge causes gas to transform into a non-equilibrium state.

13. Method according to claim 4, wherein said electrical discharge causes gas to transform into a non-equilibrium state.

14. Method according to claim 6, wherein said simultaneous reaction is maintained until said titanium oxide film with a thickness of 60 to 800 nm is formed.

15. Method according to claim 7, wherein the fluence of said neutral oxygen atoms onto said device made from NiTi alloys in said reaction chamber is between $5 \times 10^{23}$ m$^{-2}$ and $5 \times 10^{24}$ m$^{-2}$.

16. Method according to claim 1, wherein the medical device treated is a stent.

17. Method according to claim 1, wherein said leaking hydrogen gas into said reaction chamber during continuous pumping of said reaction chamber is performed such that the pressure in the said reaction chamber is between 10 and 1000 Pa.

18. Method according to claim 2, wherein said additional gas is a noble gas.

* * * * *